(12) United States Patent
Hasse et al.

(10) Patent No.: US 8,449,491 B2
(45) Date of Patent: May 28, 2013

(54) APPLICATOR HAVING EXTENDED GRIPPING FORMATIONS

(75) Inventors: Margaret Henderson Hasse, Wyoming, OH (US); Diana Lynn Gann, Lebanon, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 618 days.

(21) Appl. No.: 12/488,772

(22) Filed: Jun. 22, 2009

(65) Prior Publication Data

US 2010/0324467 A1 Dec. 23, 2010

(51) Int. Cl.
*A61F 13/26* (2006.01)
*A61F 13/32* (2006.01)
*A61F 13/30* (2006.01)

(52) U.S. Cl.
USPC .................................. 604/11; 604/15; 604/14

(58) Field of Classification Search
USPC ........................................ 604/11–18
See application file for complete search history.

(56) References Cited

U.S. PATENT DOCUMENTS

| | | | |
|---|---|---|---|
| D250,049 S * | 10/1978 | Hite, Jr. ..................... D24/141 |
| D250,663 S | 12/1978 | Koch et al. | |
| 4,573,964 A * | 3/1986 | Huffman ........................ 604/15 |
| 4,891,042 A | 1/1990 | Melvin et al. | |
| 5,738,646 A | 4/1998 | Fox et al. | |
| 5,931,803 A * | 8/1999 | Jackson ......................... 604/15 |
| 6,264,626 B1 | 7/2001 | Linares et al. | |
| 6,368,442 B1 * | 4/2002 | Linares et al. ............... 156/198 |
| 6,416,488 B1 * | 7/2002 | Jackson et al. ................. 604/15 |
| 6,432,076 B1 | 8/2002 | Wada et al. | |
| 6,685,787 B2 | 2/2004 | Linares et al. | |
| 6,890,324 B1 | 5/2005 | Jackson et al. | |
| 7,081,110 B2 * | 7/2006 | Karapasha ..................... 604/15 |
| 7,166,101 B2 | 1/2007 | Denti et al. | |
| 7,241,274 B2 * | 7/2007 | Suga ............................... 604/15 |
| 7,727,208 B2 * | 6/2010 | Lemay et al. ............. 604/385.17 |
| 7,815,594 B2 | 10/2010 | Dougherty, Jr. et al. | |
| 2003/0236485 A1 | 12/2003 | Fedyk et al. | |
| 2005/0015041 A1 | 1/2005 | Karapasha | |
| 2005/0177091 A1 | 8/2005 | Jarmon et al. | |
| 2006/0004319 A1 * | 1/2006 | Berg et al. ....................... 604/15 |
| 2008/0033337 A1 * | 2/2008 | Dougherty et al. ............. 604/15 |

(Continued)

FOREIGN PATENT DOCUMENTS

| DE | 27 55 012 A1 | 9/1977 |
| JP | 2003-3180742 A | 7/2003 |

OTHER PUBLICATIONS

PCT International Search Report dated Sep. 2, 2010.

*Primary Examiner* — Susan Su
(74) *Attorney, Agent, or Firm* — Andrew J. Hagerty; Amanda T. Barry

(57) ABSTRACT

An applicator for a feminine hygiene device. The applicator includes an insertion member that can have an outer surface, an insertion end, a withdrawal end opposite the insertion end, and a barrel region adapted to house the feminine hygiene device. In addition, the insertion member can have an indentation region extending inwardly from the outer surface and disposed between the barrel region and withdrawal end, and a shoulder region disposed between the barrel region and the indentation region. In certain embodiments, the indentation region can include one or more gripping formations protruding from the indentation region, the one or more gripping formations extending from the indentation region over at least a portion of the shoulder region.

11 Claims, 1 Drawing Sheet

U.S. PATENT DOCUMENTS

2008/0119778 A1* 5/2008 Jorgensen et al. .............. 604/14
2008/0243046 A1* 10/2008 Cettina et al. ................... 604/15
2009/0192436 A1 7/2009 Karapasha et al.
2011/0009803 A1 1/2011 Dougherty, Jr. et al.

* cited by examiner

APPLICATOR HAVING EXTENDED GRIPPING FORMATIONS

FIELD OF THE INVENTION

The present invention relates to an improved applicator for feminine hygiene devices, and more particularly, to an improved applicator for feminine hygiene devices having one or more extended gripping formations.

BACKGROUND OF THE INVENTION

Feminine hygiene devices, such as tampons and pessaries, are generally used by women within the vagina for feminine needs, such as, e.g. to absorb menstrual or other body exudates, for pelvic support, and/or for other feminine needs. Such feminine products can be inserted into the vagina digitally, such as, e.g., by using a finger, or can be inserted into the vagina by using an applicator.

Applicators typically can comprise an insertion member and a plunger. The material to be expelled from the applicator, such as an absorbent tampon or pessary, can be positioned within the insertion member. The insertion member can have a first end for insertion of the material and a second end for receipt of the plunger. To use the applicator, the consumer can grasp the insertion member, position the first end appropriately, such as, e.g., into the body, and move the plunger in the insertion member towards the first end to insert the material. Some applicators can also include a fingergrip configuration that is located on the insertion member, which can allow the consumer to more securely hold the applicator during insertion of a material into the body cavity.

Various fingergrip configurations have been proposed to facilitate the handling of the applicator and to improve the insertion experience. For example, certain applicators can include a straight fingergrip configuration, wherein the fingergrip is not indented from the remainder of the insertion member. In some instances, a straight fingergrip configuration can also include one or more gripping structures disposed proximate the withdrawal end of the insertion member, that can, for example, reduce finger slippage and provide a more secure grip. Alternatively, other applicators can include a fingergrip configuration having a reduced diameter compared to the remainder of the insertion member, such as, e.g., one or more indentation regions or a rearwardly decreasing diameter that can, for example, provide one or more tapers or shoulders demarcating the gripping region from the remainder of the insertion member. Generally, such applicators can contain one or more gripping structures disposed within the fingergrip area.

Although many different types of applicators for feminine hygiene devices have been previously described, currently available configurations are not yet optimized to facilitate applicator handling and insertion experience. As such, there remains a need for an improved applicator having a superior grip configuration and improved perception of comfort.

SUMMARY OF THE INVENTION

An applicator for a feminine hygiene device is provided. The applicator includes an insertion member. The insertion member can have an outer surface, an insertion end, a withdrawal end opposite the insertion end, and a barrel region adapted to house the feminine hygiene device. In addition, the insertion member can have an indentation region extending inwardly from the outer surface and disposed between the barrel region and withdrawal end, and a shoulder region disposed between the barrel region and the indentation region. In certain embodiments, the indentation region can include one or more gripping formations protruding from the indentation region, the one or more gripping formations extending from the indentation region over at least a portion of the shoulder region.

An applicator for a feminine hygiene device is also provided. The applicator includes an insertion member. The insertion member can have an outer surface, an insertion end, a withdrawal end opposite the insertion end, and a barrel region adapted to house the feminine hygiene device. In addition, the insertion member can have an indentation region extending inwardly from the outer surface and disposed between the barrel region and withdrawal end, and a shoulder region disposed between the barrel region and the indentation region. In certain embodiments, the indentation region can include one or more gripping formations protruding from the indentation region, the one or more gripping formations extending from the indentation region over the shoulder region and onto a portion of the barrel region proximate the indentation region.

In addition, an applicator for a feminine hygiene device is provided. The applicator includes an insertion member. The insertion member can have an outer surface, an insertion end, a withdrawal end opposite the insertion end, and a barrel region adapted to house the feminine hygiene device. In addition, the insertion member can have an indentation region extending inwardly from the outer surface and disposed between the barrel region and withdrawal end, and a shoulder region disposed between the barrel region and the indentation region. In certain embodiments, the indentation region can include a pattern of gripping formations protruding from the indentation region, the pattern of gripping formations extending from the indentation region over at least a portion of the shoulder region.

DETAILED DESCRIPTION OF THE INVENTION

Figure 1:
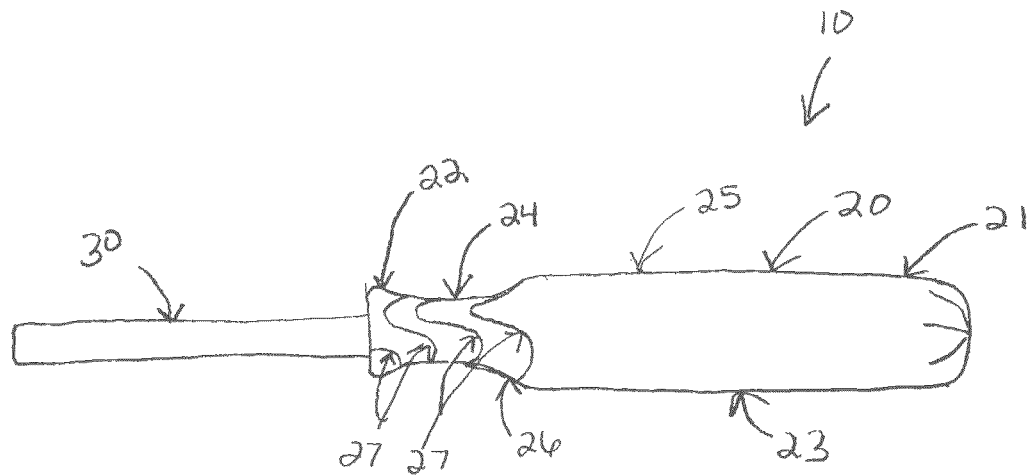
FIG. 1 is a side view of an applicator of the present invention.

Improved feminine hygiene device applicators are provided, that can, for example, provide a consumer with an improved grip and/or improved perception of comfort during use of the applicator. In certain embodiments, the feminine hygiene device applicator can include an insertion member having an indented fingergrip region. In addition, the insertion member can include one or more shoulder regions provided between the indented fingergrip region and the remainder of the insertion member. As described herein, indented fingergrip region can also include one or more gripping formations that can extend beyond the fingergrip region over at least a portion of the shoulder region, or, alternatively, in certain embodiments, over the shoulder region and at least a portion of the remainder of the insertion member. Such applicator configurations can provide an improved gripping experience and can also provide the perception of a slimmer, more comfortable applicator.

As used herein, the term "feminine hygiene device" includes absorbent articles useful for feminine needs, such as articles that typically can be intended for feminine use internally, such as, e.g., within a user's vagina. Internal feminine hygiene devices can include, for example, tampons and pessaries.

As used herein, the term "tampon" refers to any type of absorbent structure that can be inserted into the vaginal canal or other body cavity, such as, e.g., for the absorption of fluid, to aid in wound healing, and/or for the delivery of materials, such as moisture or active materials such as medicaments.

As used herein, the term "pessary" refers to any type of substantially non-absorbent structure for the purpose of reducing urine leakage and/or supporting a prolapsed uterus and/or bladder. Such pessaries can have any variety of shapes and sizes including cylinder, ovate, spherical, tubular, annual rings, "U" shaped, cup shaped, rings, cubes or donut shaped, and can function in any suitable manner, such as, e.g. by direct application of support, lever force, expansion of the device by selection of material, and/or by inflation of the device.

As used herein, the term "vaginal canal" refers to the internal genitalia of the human female in the pudendal region of the body. The terms "vaginal canal" or "within the vagina" as used herein are intended to refer to the space located between the introitus of the vagina (sometimes referred to as the sphincter of the vagina) and the cervix.

As used herein, "applicator" refers to a device or implement that facilitates the insertion of a feminine hygiene device, such as, e.g., a tampon or pessary, into an external orifice of a mammal. Exemplary applicators include telescoping, tube and plunger, and compact applicators.

As used herein, the term "insertion end" refers to the portion of the tampon or applicator including the end that is intended to enter the vaginal canal first when inserting the tampon or applicator into the vaginal canal.

As used herein, the term "withdrawal end" refers to the portion of the applicator opposite the insertion end including the end is intended to exit the vaginal canal first when the applicator is removed from the vagina.

As used herein, the term "barrel region" refers to the portion of the applicator adapted to house the feminine hygiene device. In certain embodiments, the barrel region includes the region of the applicator having the largest diameter.

As used herein, the term "indentation region" refers to the portion of the applicator adapted to provide a gripping surface that can facilitate grasping and/or holding of the applicator. In certain embodiments, the indentation region includes the region of the applicator having the smallest diameter.

As used herein, the term "shoulder region" refers to the upper region of the surface providing the slope or angle from the barrel region to the indentation region.

As used herein, the term "gripping formations" refers to raised or depressed structures provided at the fingergrip region of the applicator to assist a user in grasping the applicator. Suitable gripping formations include, e.g., projections, rings, ridges, ribs, embossments, and/or other raised surfaces.

FIG. 1 shows one embodiment of an applicator 10. The applicator 10 comprises an insertion member 20 and a plunger 30. The insertion member 20 has an insertion end 21 and a withdrawal end 22 opposite the insertion end 21. The insertion member 20 can also include a barrel region 23 adapted to contain a feminine hygiene device such as, e.g., tampon 40, and a indentation region 24 that can be provided opposite the insertion end 21, such as, e.g., proximal to the withdrawal end 22. As shown in FIG. 1, the indentation region 24 protrudes inward from an outer surface 25 of the insertion member 20. In addition, in certain embodiments, the indentation region 24 can be demarcated from the barrel region 23 of the insertion member 20, such as, e.g., by one or more shoulder regions 26. As shown in FIG. 1, indentation region 24 can, in certain embodiments, be disposed continuously about the circumference of the insertion member 20. In addition, the indentation region 24 can comprise gripping formations 27 that can protrude outward from the indentation region 24. As shown in FIG. 1, in certain embodiments, one or more gripping formations 27 can extend from the indentation region 24 over at least a portion of one or more shoulder regions 26.

Figure 2:
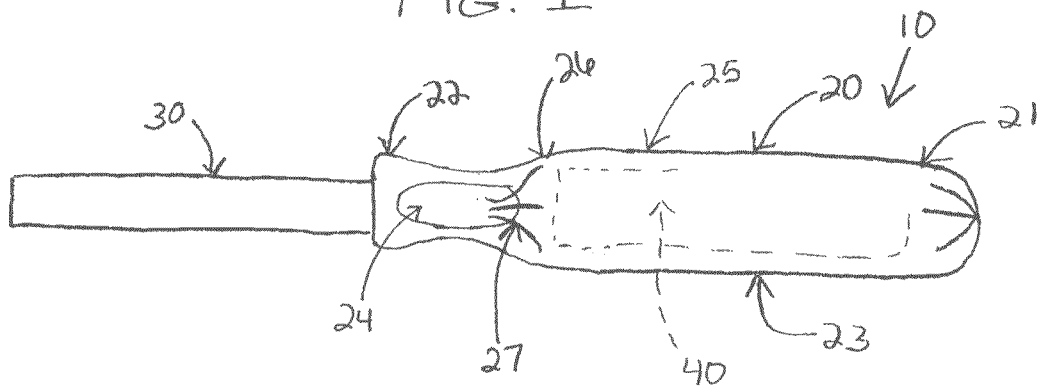
FIG. 2 is a side view of an applicator of the present invention.

FIG. 2 shows one embodiment of an applicator 10. The applicator 10 comprises an insertion member 20 and a plunger 30. The insertion member 20 has an insertion end 21 and a withdrawal end 22 opposite the insertion end 21. The insertion member 20 can also include a barrel region 23 adapted to contain a feminine hygiene device such as, e.g., tampon 40, and a indentation region 24 that can be provided opposite the insertion end 21, such as, e.g., proximal to the withdrawal end 22. As shown in FIG. 2, the indentation region 24 protrudes inward from an outer surface 25 of the insertion member 20. In addition, in certain embodiments, the indentation region 24 can be demarcated from the barrel region 23 of the insertion member 20, such as, e.g., by one or more shoulder regions 26. As shown in FIG. 2, indentation region 24 can, in certain embodiments, comprise a plurality of discrete elements disposed about the circumference of the insertion member 20. In addition, the indentation region 24 can comprise gripping formations 27 that can protrude outward from the indentation region 24. As shown in FIG. 2, in certain embodiments, one or more gripping formations 27 can extend from the indentation region 24 over one or more shoulder regions 26, and over at least a portion of barrel region 23.

Figure 3:
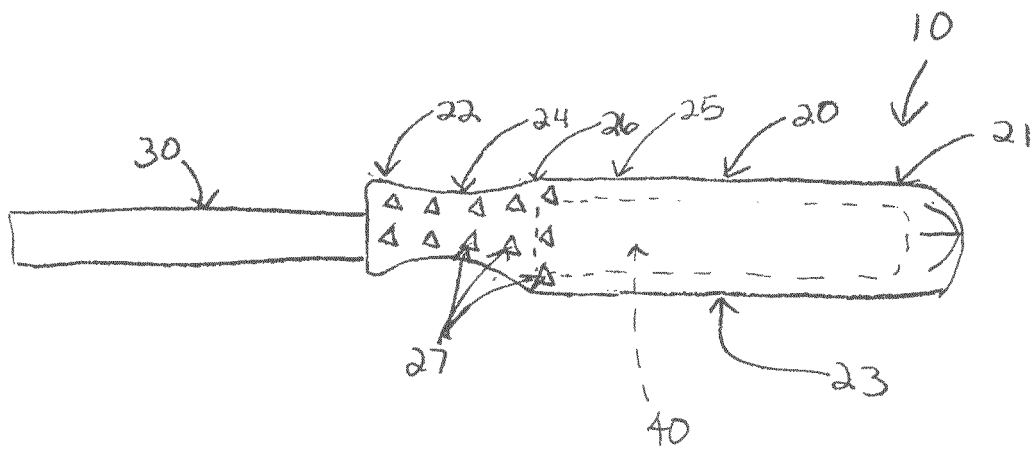
FIG. 3 is a side view of an applicator of the present invention.

FIG. 3 shows one embodiment of an applicator 10. The applicator 10 comprises an insertion member 20 and a plunger 30. The insertion member 20 has an insertion end 21 and a withdrawal end 22 opposite the insertion end 21. The insertion member 20 can also include a barrel region 23 adapted to contain a feminine hygiene device such as, e.g., tampon 40, and a indentation region 24 that can be provided opposite the insertion end 21, such as, e.g., proximal to the withdrawal end 22. As shown in FIG. 3, the indentation region 24 protrudes inward from an outer surface 25 of the insertion member 20. In addition, in certain embodiments, the indentation region 24 can be demarcated from the barrel region 23 of the insertion member 20, such as, e.g., by one or more shoulder regions 26. As shown in FIG. 3, indentation region 24 can, in certain embodiments, be disposed continuously about the circumference of the insertion member 20. In addition, the indentation region 24 can comprise gripping formations 27 that can protrude outward from the indentation region 24. As shown in FIG. 3, in certain embodiments, gripping formations 27 can be provided in a pattern, wherein the pattern can extend from the indentation region 24 over at least a portion of one or more shoulder regions 26.

As set forth herein, the gripping formations can be provided in the indention region and over at least a portion of the shoulder region and/or over the shoulder region onto at least a portion of the barrel region. Generally, the shoulder region refers to the upper region of the slope or angle from the barrel region to the indentation region, and in certain embodiments, may be further defined as the upper half of the surface having a slope or angle beginning at the barrel region and ending at the indentation region, such as, e.g., the upper half closest to the barrel region of the applicator. In addition, in certain embodiments, the shoulder region can be further defined as the upper third or upper quarter of the surface having a slope or angle beginning at the barrel region and ending at the indentation region, such as, e.g., the upper third or upper quarter closest to the barrel region of the applicator. In certain embodiments, the gripping formations can extend only over the shoulder region. Alternatively, in certain embodiments, the gripping formations can also extend over the portion of the barrel region closest to the indentation region, such as, e.g., over about 10%, over about 20%, over about 30%, or over any other suitable amount of the barrel region closest to the indention region. As such, in certain embodiments, the gripping formations do not extend to the insertion end of the applicator. In addition, in certain embodiments, the gripping formations can be provided on the barrel portion in a region where the diameter is not increasing toward the insertion end, and/or can be provided on the barrel region up to or over the maximum diameter point of the applicator.

The gripping formations can be provided in any suitable configuration, such as, e.g., longitudinal formations, waves, swirls, a substantially contiguous pattern of individual elements, a substantially contiguous pattern of joined elements, or any other suitable configuration. In certain embodiments, the application can include at least one elongated gripping formation provided within indentation region in a direction generally parallel to the longitudinal axis (L) of the applicator, wherein the at least one elongated gripping formation extends from the indentation region over at least a portion of a shoulder region of the applicator.

In addition, the indentation region can comprise any suitable shape and/or configuration that can facilitates grasping and/or holding of the applicator. For example, the indention region can be a shape and/or configuration suitable for positioning one or more of a user's fingers within the indention region. For example, in certain embodiments, the indentation region can be disposed continuously about the circumference of the insertion member. Alternatively, the indentation region can include one or more discrete elements. The indentation region can have any suitable shape and/or cross-section, such as, e.g., circular, oval, elliptical, or a cross-section having a non-arcuate perimeter, such as, e.g., a square, rectangular, triangular, polygonal, flattened, or other suitable cross-sectional shape. In certain embodiments, the indentation region can have a perimeter wherein a portion of the perimeter is arcuate and wherein a portion of the perimeter is non-arcuate, such as, e.g., an indentation region with one or more curved sides and one or more flattened sides.

The insertion member can be constructed from any suitable material. Suitable materials include, for example, paper, paperboard, cardboard, cellulose, such as, e.g. molded cellulose, or any combinations thereof, polyethylene, polypropylene, polybutylene, polystyrene, polyvinylchloride, polyacrylate, polymethacrylate, polyacrylonitrile, polyacrylamide, polyamide, nylon, polyimide, polyester, polycarbonate, polylactic acid, poly hydroxyalkanoate, ethylene vinyl acetate, polyurethane, silicone, derivatives thereof, copolymers thereof, mixtures thereof, or any suitable smooth plastic material. Examples of suitable materials are disclosed in, e.g., U.S. Pat. Nos. 5,346,468 and 5,558,631. In certain embodiments, additives can be included in the material to alter or enhance certain material properties. Suitable additives include, for example, mold release agents, slip agents, surface energy modifiers, pearlescent agents, and/or any other suitable additives. In certain embodiments, the insertion member can be coated with a substance to give it a high slip characteristic, such as, e.g., with wax, polyethylene, a combination of wax and polyethylene, cellophane, clay, mica, and other lubricants that can facilitate comfortable insertion. Alternatively, or in addition, the insertion member can include a textured surface. Texture can be provided in any suitable manner, such as, e.g., by designing texture into or adding texture to the insertion member.

In certain embodiments, the insertion member can be in the form of a spirally wound, convolutely wound or longitudinally seamed hollow tube, which can be formed from paper, paperboard, cardboard or a combination thereof. The insertion member can have one or more walls of any suitable thickness. In certain embodiments, the one or more walls can have a predetermined thickness of from about 0.1 millimeters to about 0.7 millimeter. The wall can be constructed from a single ply of material or can be formed from two or more plies that are bonded together, such as, e.g., to form a laminate. When two or more plies are utilized, some or all of the plies can be spirally wound, convolutely wound or longitudinally seamed to form an elongated cylinder. For example, in certain embodiments the wall can be constructed using a smooth thin ply of material on the outside or exterior surface that surrounds a coarser and possibly thicker ply. In embodiments where the wall contains at least three plies, the middle ply can be the thicker ply and the interior and exterior plies can be smooth and/or slippery to facilitate expulsion of the tampon and to facilitate insertion of the insertion member. The wall can contain one to four plies, although more plies can be utilized if desired.

The plies can be held together in any suitable manner, such as, e.g. by one or more adhesives, such as glue, by heat, by pressure, by ultrasonics, or by any other suitable manner for holding the plies together. The adhesive can be either water-soluble or water-insoluble. In certain embodiments, a water-soluble adhesive can be used such that the wall will quickly break apart when it is immersed in water, such as, e.g., by flushing the insertion member down a toilet.

Alternatively, the material can be overlapped into a tubular configuration, such as, for example, by spirally or convolutely winding the insertion member into a cylindrical tube. In the case of other tube construction methods such as fiber or plastic molding, or integral tube forming (e.g., thermoforming plastic) no seams may be present and the corrugations could optionally be formed as part of the tube molding or forming process.

As set forth herein, the insertion member includes an indentation region having a plurality of gripping formations, such as, e.g., projections, rings, ridges, ribs, embossments, depressions, grooves, and/or other gripping structures. The gripping formations can be provided in any suitable manner, such as, e.g., by the addition of material, and/or by impressing, such as, e.g., by embossing, or compressing the surfaces. In certain embodiments, the indentation region can include one or more flattened sides and/or one or more spaces for a decorative marking or a character, such as, e.g., an embossed and/or printed marking or character. In addition, or alternatively, the surfaces of the indentation region can include a material that can provide a frictional resistance for the user's fingers during the insertion of the tampon applicator into the body. Suitable materials that can provide friction include, for example, abrasive materials, high wet coefficient of friction materials, pressure sensitive adhesives, or any combinations thereof.

The gripping formations can have any suitable dimensions. In certain embodiments, the gripping formations can be elongated, such as, e.g., having a length greater than the width. In addition or alternatively, the gripping formations can have a height extending outward from the surface of the insertion member. In certain embodiments, the gripping formations can have a height greater than about 0.1 mm, such as, e.g., a height from about 0.1 mm to about 0.8 mm, such as, e.g. a height from about 0.1 mm to about 0.6 mm, such as, e.g., a height from about 0.15 mm to about 0.5 mm, such as, e.g. a height from about 0.2 mm to about 0.4 mm, such as, e.g., a height from about 0.2 mm to about 0.3 mm, or any other suitable height.

In certain embodiments, the gripping formations can have varying heights along the length of the applicator. For example, in certain embodiments, the gripping formations can be higher in the indentation region and lower on the shoulder region and/or barrel region. Alternatively, in certain embodiments, the gripping formations can be higher on the shoulder and/or barrel and lower in the indentation region.

The gripping formations can be provided in the indentation region in any suitable location. In certain embodiments, the gripping formations can form a design, such as, e.g., a pattern. The gripping formations can be arranged to form a perceived pattern, such as, e.g., a line, a broken line, waves, swirls, a ring, and/or a broken ring. For example, in certain embodiments, a plurality of gripping formations can be arranged to form a series of waves, such as, e.g., one or more waves having a crest provided within the indentation region and a trough provided over the shoulder region and/or onto the barrel region As shown herein, in certain embodiments, the gripping formations can include elongated ridges, such as, e.g., ridges having a length and a width, with the length being greater than the width. In certain embodiments, a ridge can have a length that can be perpendicular to the longitudinal axis of the applicator. In addition, or alternatively, one or more elongated ridges can be connected to form waves, swirls, or other suitable patterns.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An applicator for a feminine hygiene device comprising:
   an insertion member;
   the insertion member having an outer surface, an insertion end, a withdrawal end opposite the insertion end, and a barrel region adapted to house the feminine hygiene device, the insertion member having an indentation region extending inwardly from the outer surface and disposed between the barrel region and withdrawal end, the insertion member further having a shoulder region disposed between the barrel region and the indentation region;
   the indentation region comprising one or more gripping formations protruding from the indentation region, the one or more gripping formations extending from the indentation region over the shoulder region and onto a portion of the barrel region proximate the indentation region.

2. The applicator of claim 1, wherein the indentation region is disposed continuously about the circumference of the insertion member.

3. The applicator of claim 1, wherein the indentation region comprises one or more discrete elements.

4. The applicator of claim 1, wherein the one or more gripping formations protrude outwardly from the indentation region.

5. The applicator of claim 1, wherein the one or more gripping formations are elongated gripping formations originating in the indentation region and terminating in the barrel region.

6. The applicator of claim 5, wherein the elongated gripping formations extend substantially parallel to a longitudinal axis of the applicator.

7. The applicator of claim 5, wherein the elongated gripping formations are in the form of lines, swirls, or waves.

8. The applicator of claim 1, wherein the one or more gripping formations extend over less than 30% of the barrel region.

9. The applicator of claim 1, wherein the applicator is a tampon applicator.

10. An applicator for a feminine hygiene device comprising:
    an insertion member;
    the insertion member having an outer surface, an insertion end, a withdrawal end opposite the insertion end, and a barrel region adapted to house the feminine hygiene device, the insertion member having an indentation region extending inwardly from the outer surface and disposed between the barrel region and withdrawal end, the insertion member further having a shoulder region disposed between the barrel region and the indentation region;
    the indentation region comprising one or more gripping formations protruding from the indentation region, the one or more gripping formations extending from the indentation region over the shoulder region and onto a portion of the barrel region proximate the indentation region;
    wherein the one or more gripping formations extend over less than 20% of the barrel region.

11. The applicator of claim 10, wherein the one or more gripping formations extend over less than 10% of the barrel region.

* * * * *